US00PP09092P

United States Patent [19]

Losely

[11] Patent Number: Plant 9,092

[45] Date of Patent: Mar. 28, 1995

[54] SHADBLOW SERVICEBERRY PLANT NAMED 'GLENN FORM'

[75] Inventor: Edward Losely, Perry, Ohio

[73] Assignee: Herman Losely & Son, Inc., Perry, Ohio

[21] Appl. No.: 159,822

[22] Filed: Dec. 1, 1993

[51] Int. Cl.[6] ..... A01H 5/00

[52] U.S. Cl. ..... Plt./51.1

[58] Field of Search ..... Plt. 51.1

[56] References Cited

U.S. PATENT DOCUMENTS

P.P. 7,072 12/1989 Flemer ..... Plt./51.1

*Primary Examiner*—James R. Feyrer

*Attorney, Agent, or Firm*—Renner, Otto, Boisselle & Sklar

[57] ABSTRACT

A shadblow serviceberry plant named Glenn Form, a large shrub characterized by its upright and dense branching habit, dense foliage, regular growth form, and freedom from defoliating leaf diseases, making it particularly suitable for use as a hedge or screen.

4 Drawing Sheets

1

The present invention relates to a new and distinct variety of shadblow serviceberry plant, botanically known as *Amelanchier canadensis*, and known by the cultivar name Glenn Form.

This new cultivar was discovered by me as a seedling selected from a large planting of seedlings in a cultivated area in Lake County, Ohio. This new cultivar stood out among its sister seedlings by virtue of its upright and dense branching habit and symmetrical growth form, the typical seedling being more broad spreading, open, and irregular in its branching habit.

Asexual reproduction by tissue culture at Perry in Lake County, Ohio has reproduced the unique features of the new cultivar described hereafter through successive propagations.

The growth habit of Glenn Form is that of a large shrub, having an ultimate height and spread of 1½ to 6 meters. In vegetatively propagated plants of Glenn Form, typically 3 or more stems arise from the crown, diverge at first because of competition, and soon re-orient their growth in a vertical direction. Secondary stems and branches from these grow in a vertical direction. The angle described by the outer stems of a 2½ meter tall nursery specimen is 45°–50°. Glenn Form has been vegetatively propagated by tissue culture, and plants produced in this manner consistently and uniformly exhibit the distinctive characteristics of the original selected seedling.

Although Glenn Form will grow well on shaded sites, growth is more open and less dense under such conditions. Consequently for use as a hedge or screen, Glenn Form should be grown in full sun.

The flowers and fruits of Glenn Form do not differ markedly from those typical of the species, except that the fruits are very sparsely borne. Less than 10% of inflorescences produce any mature fruit, and on those that do, only 2–3 fruits develop per raceme. In each fruit that develops, only 2–4 out of a potential 12 seeds are produced. The reasons for this lack of fertility are not known. Because sparse fruiting has been displayed in mixed plantings of Glenn Form with other seedlings of its species and cultivars of other serviceberry species which bloom at the same time and would provide ample opportunities for cross pollination, this is believed to be a consistent characteristic of this variety. Since fruits of other serviceberry species are taken so rapidly by birds

2 as they ripen, the display of fruit is not considered a significant ornamental characteristic of shadblow serviceberry palnts. The sparse production of fruit by Glenn Form is an advantage because of its attractiveness to birds and the resultant soiling of sidewalks, structures and vehicles as a result of their feeding will be minimized.

The density and growth form of Glenn Form make it eminently suited for use as a hedge or screen. Further, the natural form of Glenn Form significantly reduces the labor required to maintain it as an acceptable hedge or screen. For example, the specimen illustrated in FIG. 1 of the accompanying drawing was produced with no shearing or trimming.

The vegetative characteristics of Glenn Form are essentially similar to that of the species. However, the leaves of Glenn Form are substantially unaffected by powdery mildew, remaining clean and attached when other plants of this species are becoming defoliated. Fall leaf color is a mixture of bright red and green, yielding a mottled effect.

The following characteristics distinguish Glenn Form from other shadblow serviceberry plants:

1. Glenn Form has an upright and dense branching habit, dense foliage, regular growth form, and freedom from defoliating leaf diseases, which makes it particularly suitable for use as a hedge or screen.

2. In comparison to White Pillar disclosed in U.S. Plant Pat. No. 7,072, Glenn Form is upright but not columnar in habit, with an ultimate height of 4½ to 6 meters, and has an internode spacing that is very tight, making it a dense foliage plant that is particularly suitable as a hedge or visual screen. White Pillar, on the other hand, is columnar in habit, with an ultimate height of approximately 6 to 9 meters, and has a much wider internode spacing which gives it a more open look, making it more suitable for a windbreak or specimen tree.

Referring now more particularly to the accompanying drawing.

Figure 1:
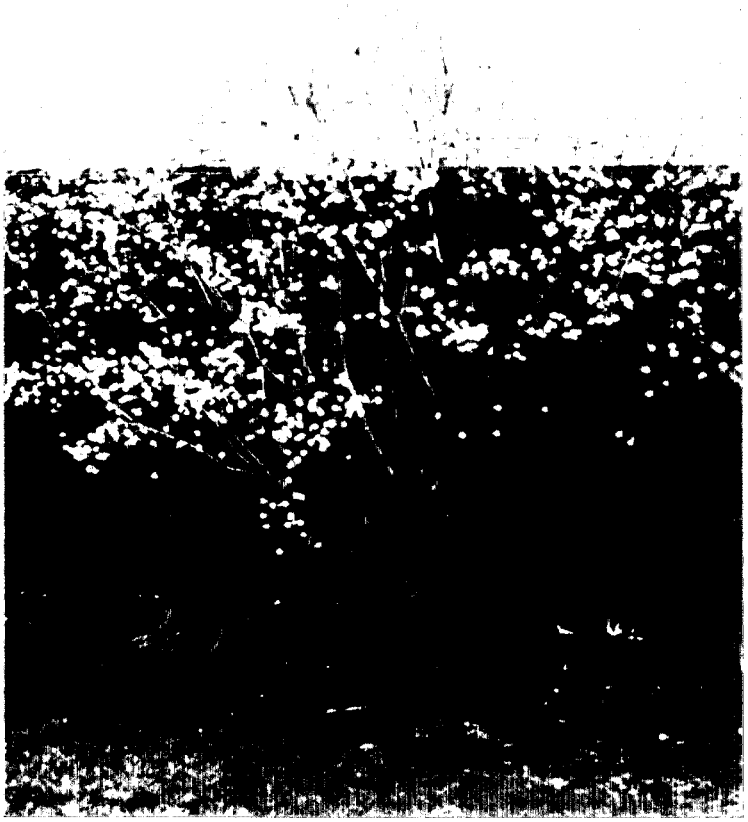
FIG. 1 is a colored photograph illustrating in perspective view the overall appearance of the cultivar Glenn Form in early spring during flowering.
Figure 2:
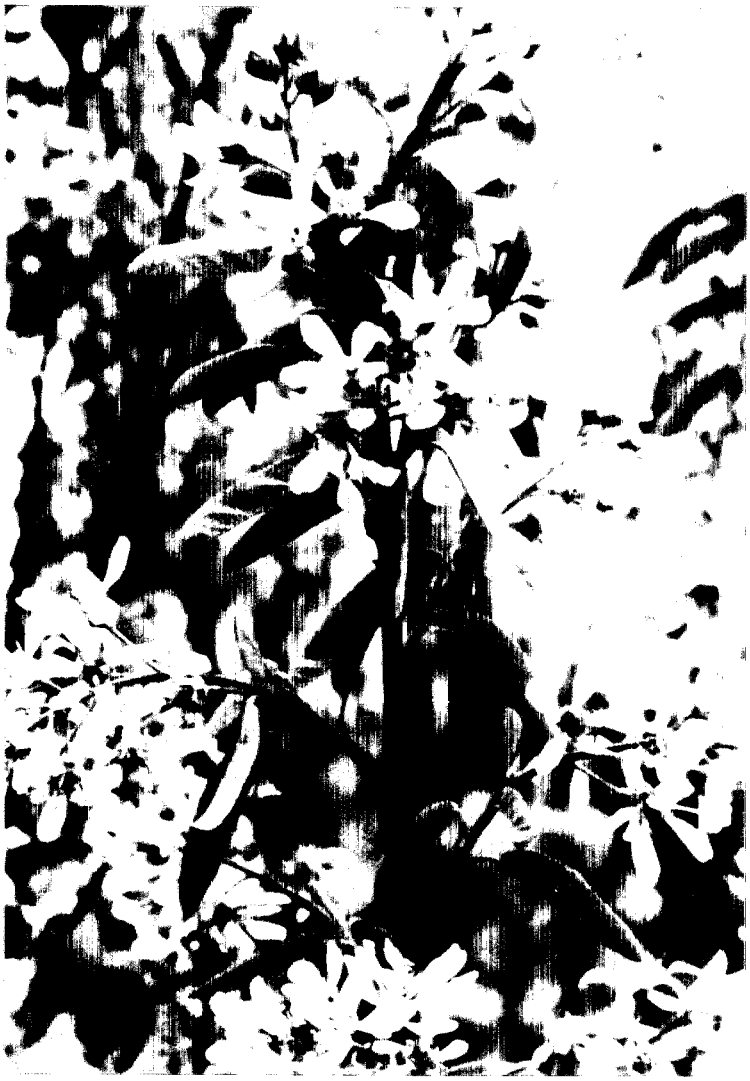
FIG. 2 is a colored photograph illustrating a close-up view of the flowers of Glenn Form.
Figure 3:
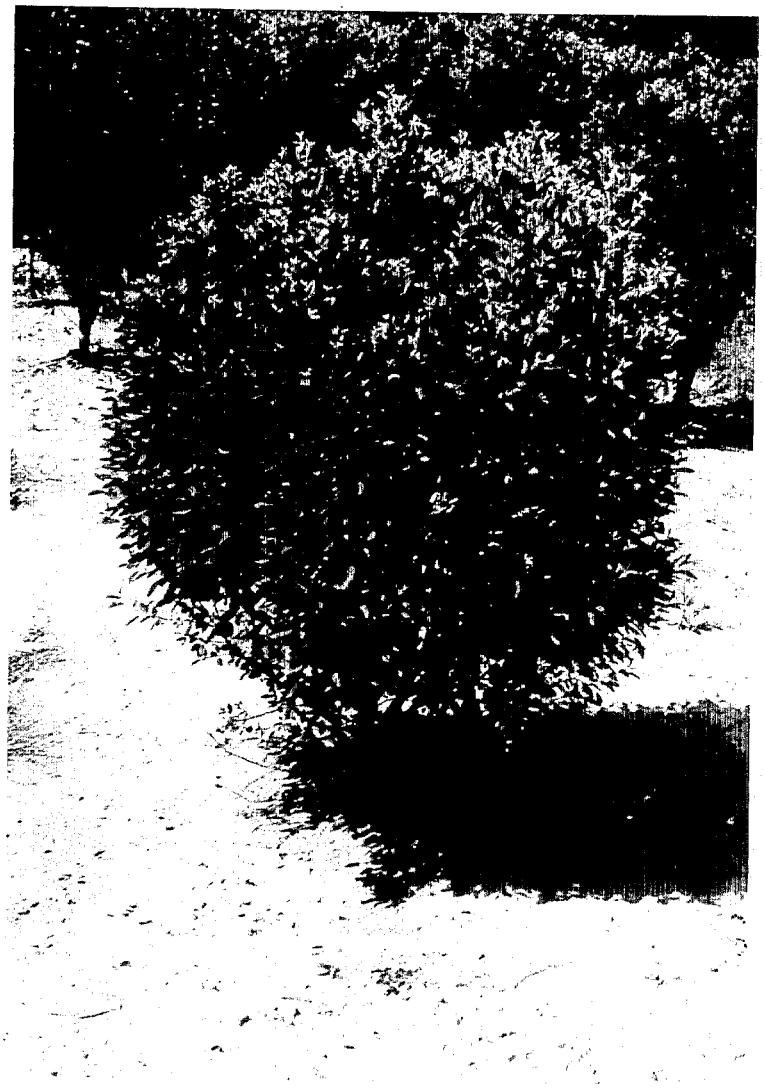
FIG. 3 is a colored photograph illustrating in perspective view the overall appearance of Glenn Form in full leaf during the summer months.
Figure 4:
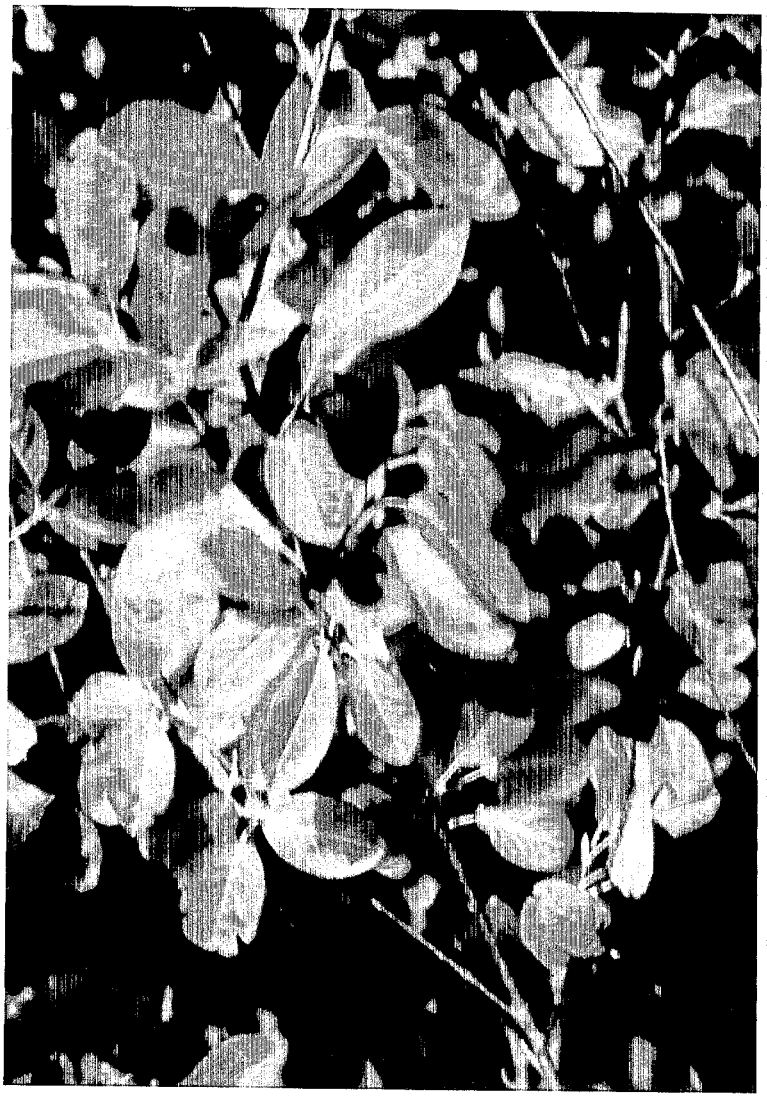
FIG. 4 is a colored photograph illustrating a close-up view of the leaves of Glenn Form in the fall.

All four drawing figures show the colors as true as is reasonably possible to obtain in colored reproductions of this type.

The following is a detailed description of my new and distinct variety of shadblow serviceberry produced and grown outdoors at Perry, in Lake County, Ohio. In all cases where color is different from other known shadblow serviceberry plants and is considered a distinguishing feature of this new variety, color references are made to The Royal Horticulture Society Colour Chart.

Parentage: Unknown—grown from commercial seed of *Amelanchier canadensis.*

Form/Size: Large shrub (to 5 meters tall and wide) of symmetrical, upright form and dense growth.

Hardiness: Hardy in USDA Hardiness Zone 4.

Growth rate: Moderate—A specimen 4 years old produces approximately 30 cm. of new growth in one year in Lake County, Ohio.

Stems: Smooth, light gray in color.

Branches: Thin and smooth, with abundant lenticels, medium brown (RHS Brown Group 200C). 1–2 years twigs covered with a waxy bloom which later weathers off to reveal brown color. Internode length 10 to 20 mm.

Leaves: Ovate, 4–5 cm. in length, 2–2.5 cm. wide. Upper surface of leaves glabrous, color Green Group 137A, with a sheen. Lower surfaces of expanding leaves are pilose, becoming glabrous except on midrib, color Green Group 138A. Fall color Red Group 43A mottled with green. Margins are serrulate. Petiole 5–10 mm. long, eglandular.

Flowers: Borne in upright racemes, 10–12 flowers per 3.5 cm. long raceme, in late April/early May in Lake County, Ohio. Individual flowers are 5-petalled, with white petals approximately 8 mm. long. Flowers are abundant, and have no fragrance.

Fruits: Sparsely borne, developing from a very few inflorescences, and only 2–3 fruits at most on a single raceme. Fruits are pomes, 7–8 mm. long and 9–10 mm. in diameter, with a persistent calyx. Fruits covered with a waxy bloom, changing from green to Red Group 45B to Red-Purple Group 59A. Fruits ripen 3rd–4th week in June. An individual fruit typically contains 2–4 fully developed seeds out of a potential 12 seeds.

I claim:

1. A shadblow serviceberry plant named Glenn Form, as described and illustrated, a large shrub characterized by its upright and dense branching habit, dense foliage, regular growth form, and freedom from defoliating leaf diseases.

* * * * *